(12) United States Patent
Sanders et al.

(10) Patent No.: US 8,120,207 B2
(45) Date of Patent: Feb. 21, 2012

(54) NANOSECOND PULSE GENERATOR WITH A PROTECTOR CIRCUIT

(75) Inventors: Jason Sanders, Los Angeles, CA (US); Andras Kuthi, Thousand Oaks, CA (US); Martin A. Gundersen, San Gabriel, CA (US); William Henry Moore, Canoga Park, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/703,078

(22) Filed: Feb. 9, 2010

(65) Prior Publication Data

US 2010/0156195 A1 Jun. 24, 2010

Related U.S. Application Data

(63) Continuation of application No. 12/471,229, filed on May 22, 2009.

(60) Provisional application No. 61/128,708, filed on May 23, 2008.

(51) Int. Cl.
*H03K 3/00* (2006.01)

(52) U.S. Cl. .................................................. 307/108

(58) Field of Classification Search .................. 307/108; 361/112
See application file for complete search history.

(56) References Cited

U.S. PATENT DOCUMENTS

| | | | |
|---|---|---|---|
| 6,426,666 B1 | 7/2002 | Li et al. | |
| 6,831,377 B2 | 12/2004 | Yampolsky et al. | |
| 7,767,433 B2 * | 8/2010 | Kuthi et al. | 435/285.2 |
| 7,817,396 B2 * | 10/2010 | Tao et al. | 361/112 |
| 2005/0218423 A1 | 10/2005 | Shimizu et al. | |
| 2006/0062074 A1 | 3/2006 | Gundersen et al. | |
| 2007/0031959 A1 | 2/2007 | Kuthi et al. | |
| 2008/0231337 A1 | 9/2008 | Krishnaswamy et al. | |
| 2010/0038971 A1 | 2/2010 | Sanders et al. | |

OTHER PUBLICATIONS

Barth RF. 1998. Rat brain tumor models in experimental neuro-oncology: the 9L, C6, T9, F98, RG2 (D47), RT-2 and CNS-1 gliomas. J Neurooncol. 36(1): pp. 91-102.

Bier M. et al. 1999. Kinetics of Sealing for Transient Electropores in Isolated Mammalian Skeletal Muscle Cells, Bioelectromagnetics, v20, pp. 194-201.

(Continued)

*Primary Examiner* — Michael Rutland Wallis
(74) *Attorney, Agent, or Firm* — McDermott Will & Emery LLP

(57) ABSTRACT

This invention relates to a pulse generator circuit for delivering a short high current pulse to a load. This pulse generator comprises a junction recovery diode, a switch, a first resonant circuit and a second resonant circuit. The diode may be configured to store charges in its depletion layer when there is a forward flow of a current and to rapidly switch open after the depletion layer is discharged by a reverse flow of a current. After the diode rapidly switch opens, the pulse generator may provide a reverse current to the load. This pulse generator may be configured to generate at least one pulse that is having a length of no more than 100 nanoseconds at the full-width-at-half-maximum and an amplitude of at least 1 kilovolt. Electrodes may be connected to the pulse generator to deliver one pulse or plurality of pulses to biological cells such as tumor cells.

27 Claims, 7 Drawing Sheets

OTHER PUBLICATIONS

Borner M. et al. 1994. The detergent Triton X-100 induces a death pattern in human carcinoma cell lines that resembles cytotoxic lymphocyte-induced apoptosis. FEBS Lett. 353: pp. 129-132.

Cole MJ et al. 2001. Time-domain whole-field fluorescence lifetime imaging with optical sectioning; Journal of Microscopy, vol. 203, Pt. 3, Sep. 2001, pp. 246-257.

Cossarizza A et al. 2001. Chapter 21 Analysis of Mitochondria during Cell Death. In Methods in Cell Biology, vol. 63, pp. 467-486.

Craft CM et al. 1998. PhLPs and PhLOPs in the phosducin family of G beta gamma binding proteins. American Chemical Society, Biochemistry 37: pp. 15758-15772.

Cubeddu R et al. 2002. Time-resolved fluorescence imaging in biology and medicine; Topical Review; Institute of Physics Publishing, J. Phys.D; Appl.Phys, 35: pp. R61-R76.

DeAngelis LM 2001. Brain Tumors. New England Journal of Medicine, v. 344: pp. 114-123.

DeBruin KA et al. 1999. Modeling electroporation in a single cell. I. Effects of field strength and rest potential. Biophysical Journal, vol. 77, Sep. 1999: pp. 1213-1224.

Frank K et al. 1998. High power pseudospark and BLT switches. IEEE Trans. Plasma Science 16 (2): pp. 317-323.

Freeman SA et al. 1994. Theory of electroporation of planar bilayer membranes: predictions of the aqueous area, change in capacitance, and pore-pore separation. Biophysical Journal, vol. 67, Jul. 1994: pp. 42-56.

Garon EB et al. 2007 In Vitro and In Vivo Evaluation and a Case Report of Intense Nanosecond Pulsed Electric Field as a Local Therapy for Human Malignancies. Int. J. Cancer, vol. 121: pp. 675-682.

Gilbert RA et al. 1997. Novel electrode designs for electrochemotherapy. Biochimica et Biophys. Acta vol. 1334, pp. 9-14.

Gotoh T et al. 2002. Nitric Oxide-induced Apoptosis in RAW 264.7 Macrophages I s Mediated by Endoplasmic Reticulum Stress Pathway Involving ATF6 and CHOP. J. Biol. Chem. vol. 277, No. 14, Apr. 2002: pp. 12343-12350.

Grekhov IV et al. 1983. Formation of Nanosecond High-Voltage Drop Across Semiconductor Diodes with Voltage Recovery by a Drift Mechanism. Soy. Tech Phys. Lett., vol. 9, No. 4: pp. 188-189.

Grekhov, IV et al. 2000 Physical Basis for High-Power Semiconductor Nanosecond Opening Switches. IEEE Transactions on Plasma Science, vol. 28: pp. 1540-1544.

Grekhov IV et al. 2005. Nanosecond Semiconductor Diodes for Pulsed Power Switching. Physics-Uspekhi, vol. 48, No. 7: pp. 703-712.

Gundersen M et al. 2004. Nanosecond Pulse Generator Using a Fast Recovery Diode. IEEE 26th Power Modulator Conference, 2004, pp. 603-606.

Hemker RG et al. 1999. Development of a parallel code for modeling plasma based accelerators. IEEE Particle Accelerator Conference 5: pp. 3672-3674.

Hewlett Packard. 1984. Application Note 918, Pulse and Waveform Generation with Step Recovery Diodes. Oct. 1984. 22 pages.

International Search Report for PCT Application Ser. No. PCT/US09/45073, mailed on Dec. 18, 2009.

Joshi RP et al. 2000. Electroporation dynamics in biological cells subjected to ultrafast electrical pulses: a numerical simulation study, Physical Review E, vol. 62, Jul. 2000: pp. 1025-1033.

Kirkman GF et al. 1986. Low pressure, light initiated, glow discharge switch for high power applications. Appl. Phys. Lett., vol. 49, Sep. 1986: pp. 494-495.

Kotnik T et al. 2000. Theoretical evaluation of the distributed power dissipation in biological cells exposed to electric fields, Bioelectromagnetics, vol. 21: pp. 385-394.

Kotov, YuA et al. A 1993. Novel Nanosecond Semiconductor Opening Switch for Megavolt Repetitive Pulsed Power Technology: Experiment and Applications. In Proceedings of the 9th Int. IEEE Pulsed Power Conference, Albuquerque, NM, 1993, pp. 134-139.

Li A et al. 2002. Retinoic acid upregulates cone arrestin expression in retinoblastoma cells through a Cis element in the distal promoter region. Invest Ophthalmol Vis Sci., vol. 43, No. 5, May 2002: pp. 1375-1383.

Li A et al. 2003. Gene expression networks underlying retinoic acid-induced differentiation of human retinoblastoma Cells Invest Ophthalmology & Vision Science, vol. 44, No. 3, Mar. 2003: pp. 996-1007.

Lyubutin SK et al. 1997. Repetitive Nanosecond All-Solid-State Pulsers Based on SOS Diodes. In IEEE 11th International Pulsed Power Conference, Baltimore, MD: pp. 992-998.

Marcu L et al. 1999. Photobleaching of arterial fluorescent compounds: characterization of elastin, collagen, and cholesterol time-resolved spectra during prolonged ultraviolet irradiation, Photochem. Photobiol., vol. 69, No. 6: pp. 713-721.

Marszalek P et al. 1990. Schwan equation and transmembrane potential induced by alternating electric field, Biophysical Journal, vol. 58, Oct. 1990: pp. 1053-1058.

Maytin EV et al. 2001. Stress-Inducible Transcription Factor CHOP/gadd153 Induces Apoptosis in Mammalian Cells via p38 Kinase-Dependent and —Independent Mechanisms. Exp. Cell Res., vol. 267: pp. 193-204.

Moll, JL et al. 1969. Physical Modeling of the Step Recovery Diode for Pulse and Harmonic Generation Circuits. In Proceedings of the IEEE, vol. 57, No. 7, Jul. 1969: pp. 1250-1259.

Pogue BW et al. 2001. In vivo NADH Fluorescence Monitoring as an Assay for Cellular Damage in Photodynamic Therapy; Photochemistry and Photobiology, vol. 74, No. 6, Oct. 2001: pp. 817-824.

Polevaya Y et al. 1999. Time domain dielectric spectroscopy study of human cells. II. Normal and malignant white blood cells. Biochim. Biophys. Acta., vol. 1419: pp. 257-271.

Rukin, SN. 1999. High-Power Nanosecond Pulse Generators Based on Semiconductor Opening Switches (Review). Instruments and Experimental Techniques, vol. 42, No. 4: pp. 439-467.

Sanders J. et al. 2008. Broadband Power Measurement of High-Voltage, Nanosecond Electric Pulses for Biomedical Applications. IEEE International Power Modulator Conference, Las Vegas, NV, 2008, pp. 350-353.

Schoenbach KH et al. 1997. The Effect of Pulsed Electric Fields on Biological Cells: Experiments and Applications, IEEE Transactions on Plasma Science, vol. 25, Apr. 1997: pp. 284-292.

Tang T. et al. 2007. Diode Opening Switch Based Nanosecond High Voltage Pulse Generators for Biological and Medical Applications. IEEE Transactions on Dielectrics and Electrical Insulation, vol. 14, No. 4: pp. 878-883.

Wakita M et al. 1995. Some Characteristics of the Fluorescence Lifetime of Reduced Pyridine Nucleotides in Isolated Mitochondria, Isolated Hepatocytes, and Perfused Rat Liver In Situ. J. Biochem., vol. 118: pp. 1151-1160.

Wang F et al. 2005. Solid-State High Voltage Nanosecond Pulse Generator. IEEE Pulsed Power Conference, pp. 1199-1202.

Watanabe K et al. 2002. Feasibility and limitations of the rat glioma model by C6 gliomas implanted—at the subcutaneous region. Neurol. Res., vol. 24, No. 5, Jul. 2002: pp. 485-490.

Weaver JC et al. 1996. Theory of Electroporation: A Review. Bioelectrochemistry and Bioenergetics, vol. 41: pp. 135-160.

Webb SED et al. 2002. A wide-field time-domain fluorescence lifetime imaging microscope with optical sectioning. Review of Scientific Instruments, vol. 73, No. 4, Apr. 2002: pp. 1898-1907.

Weiss A et al. 1984. The Role of T3 surface molecules in the activation of human t cells: a two-stimulus requirement for IL 2 production reflects events occurring at a pre-translational level. The Journal Immunology, vol. 133, No. 1, Jul. 1984: pp. 123-128.

Zhu X et al. 2000. The carboxyl terminal domain of phosducin functions as a transcriptional activator. Biochemical and Biophysical Research Communications, vol. 270: pp. 504-509.

Zhu X et al. 2002. Mouse Cone Arrestin Gene Characterization: Promoter Targets Expression to Cone Photoreceptors. FEBS Letters, vol. 425: pp. 116-122.

Non-Final Office Action, dated May 4, 2011, for U.S. Appl. No. 12/471,229, filed May 22, 2009, entitled "Nanosecond Pulse Generator" (Published as US 2010/0038971 A1, Feb. 18, 2010).

* cited by examiner

NANOSECOND PULSE GENERATOR WITH A PROTECTOR CIRCUIT

CROSS-REFERENCE TO RELATED APPLICATIONS

This application is a continuation of U.S. application Ser. No. 12/471,229, filed May 22, 2009, entitled "Nanosecond Pulse Generator," which claims priority to U.S. Provisional Application Ser. No. 61/128,708, filed May 23, 2008, entitled "Nanosecond Aircore Pulse Generator with Scalable Pulse Amplitude." The entire content of both applications is incorporated herein by reference.

STATEMENT REGARDING FEDERALLY SPONSORED RESEARCH

This invention was made with government support under Contract Nos. F49620-01-1-0495 and F49620-01-1-0387 awarded by the U.S. Air Force Office of Scientific Research. The government has certain rights in the invention.

FIELD OF THE INVENTION

This invention relates to pulse generators and, more particularly, to pulse generators that may be used for electroperturbation of biological cells.

BACKGROUND OF THE INVENTION

Ultra-short, high-field strength electric pulses may be used in the electroperturbation of biological cells. For example, these electric pulses may be used in treatment of human cells and tissue including tumor cells, such as basal cell carcinoma, squamous cell carcinoma and melanoma. For in detail discussion of such applications, for example, see, Garon et al. "In Vitro and In Vivo Evaluation and a Case Report of Intense Nanosecond Pulsed Electric Field as a Local Therapy for Human Malignancies", Int. J. Cancer, vol. 121, 2007, pages 675-682.

The voltage induced across a cell membrane may depend on the pulse length and pulse amplitude. Pulses longer than about 1 microsecond may charge the outer cell membrane and lead to opening of pores, either temporarily or permanently. Permanent openings may result in cell death.

Pulses much shorter than about 1 microsecond may affect the cell interior without adversely affecting the outer cell membrane. Such shorter pulses with a field strength varying in the range of 1 MV/m to 10 MV/m may trigger apoptosis or programmed cell death. Higher amplitude and shorter electric pulses are useful in manipulating intracellular structures such as nuclei and mitochondria.

Spark gap switched transmission lines have been used to generate ultra-short pulses. However, they may be physically large and have only a low repetition rate. They may also have only a relatively short lifetime, and provide erratic pulses with a large amount of jitter. The transmission line capacitance may also need to be charged rapidly in order to overvolt the spark gap to meet a fast rise time requirement.

Radio frequency metal-oxide semiconductor field effect transistor (MOSFET) switched capacitors have also been used to generate ultra-short pulses. However, MOSFET switched capacitors may not be able to generate pulses with lengths narrower than 15-20 nanoseconds. This may be due to complications of MOSFET driving circuits and inherent limitations of many MOSFET devices.

Nanosecond high voltage based pulse generators based on diode opening switches have also been proposed for biological and medical applications. For example see: Gundersen et al. "Nanosecond Pulse Generator Using a Fast Recovery Diode", IEEE 26th Power Modulator Conference, 2004, pages 603-606; Tang et al. "Solid-State High Voltage Nanosecond Pulse Generator," IEEE Pulsed Power Conference, 2005, pages 1199-1202; Tang et al. "Diode Opening Switch Based Nanosecond High Voltage Pulse Generators for Biological and Medical Applications", IEEE Transactions on Dielectrics and Electrical Insulation, Vol. 14, No. 4, 2007, pages 878-883; Yampolsky et al., "Repetitive Power Pulse Generator With Fast Rising Pulse" U.S. Pat. No. 6,831,377; Gundersen et al., "Method for Intracellular Modifications Within Living Cells Using Pulsed Electric Fields", U.S. Patent Publication No. 2006/0062074; Kuthi et al., "High Voltage Nanosecond Pulse Generator Using Fast Recovery Diodes for Cell Electro-Manipulation", U.S. Patent Publication No. 2007/0031959; and Krishnaswamy et al., "Compact Subnanosecond High Voltage Pulse Generation System for Cell Electro-Manipulation", U.S. Patent Publication No. 2008/0231337.

The diode opening switches may operate at two different modes. The first mode is called junction recovery (JR) mode and the second mode silicon opening switch (SOS) mode. For in detail description of diode opening switches, for example, see: Moll et al., "Physical Modeling of the Pulse and Harmonic Step Recovery Diode for Generation Circuits", Proceedings of the IEEE, vol. 57, no. 7, 1969, pages 1250-1259; Hewlett Packard Application Note 918, "Pulse and Waveform Generation with Step Recovery Diodes"; Kotov et al., "A Novel Nanosecond Semiconductor Opening Switch for Megavolt Repetitive Pulsed Power Technology: Experiment and Applications," Proc. 9th Int. IEEE Pulsed Power Conf., Albuquerque, N. Mex., 1993, pages 134-139; Lyubutin et al., "Repetitive Nanosecond All-Solid-State Pulsers Based on SOS Diodes", IEEE 11th Intern. Pulsed Power Conf., Baltimore, Md., 1997, pages 992-998; Rukin, "High-Power Nanosecond Pulse Generators Based on Semiconductor Opening Switches", Instruments and Experimental Techniques, vol. 42, No. 4, 1999, pages 439-467; and Grekhov et al., "Physical Basis for High-Power Semiconductor Nanosecond Opening Switches," IEEE Transactions on Plasma Science, vol. 28, 2000, pages 1540-1544.

SUMMARY

This invention relates to a pulse generator circuit for delivering a short high current pulse to a load. This pulse generator comprises a junction recovery diode, a switch, a first resonant circuit and a second resonant circuit.

These components of the electric circuit may be configured as follows. The diode may be configured to store charges in its depletion layer when there is a forward flow of a current and to rapidly switch open after the depletion layer is substantially discharged by a reverse flow of a current. The switch may be configured to allow storage of energy from a source when it is opened and to allow the forward current flow after it is closed. The first resonant circuit may be configured to store energy from a source when the switch is opened and to provide the forward flow of the current through the diode after the switch is closed, thereby charging the depletion layer of the diode. The second resonant circuit may be configured to store the energy transferred from the first resonant circuit after the switch is closed and to provide the reverse flow of the current through the diode until the depletion layer of the diode is substantially discharged, thereby causing the diode to rapidly switch open, and thereafter to provide a reverse current to the load.

This pulse generator may be configured to cause the charges stored in the depletion layer of the diode to be substantially discharged when the peak current flowing through the second resonant circuit is substantially higher than the peak current that previously flowed through the first resonant circuit. The pulse generator may even be configured to cause the charges stored in the depletion layer of the diode to be substantially discharged when the ratio of the peak of the reverse flow of the current to the peak of the forward flow of the current is substantially approaching to two.

A diode that has suitable charge storage characteristics and a very short snap-off time may be suitable for the pulse generators of the instant invention. For example, the diode of this pulse generator may be a diode operating in a junction recovery mode. This diode may also be a diode operating in a silicon opening switch mode. This diode may even be a combination of diodes operating in the junction recovery mode or the silicon opening switch mode.

The diode of the instant invention may have a junction recovery time longer than 10 nanoseconds. This junction recovery time may even be longer than 25 nanoseconds. This diode may be configured to have a snap-off time shorter than 10 percent of its junction recovery time. This diode may even be configured to store charges in its depletion layer with an amount higher than one micro-coulomb.

The first resonant circuit of the pulse generator of the instant invention or the second resonant circuit may comprise an inductor. This inductor may be an air-core inductor, a linear-magnetic-core inductor, a saturable-magnetic-core inductor or combinations thereof. All possible combinations of these inductor types may be useful for construction of the inductor of the first resonant circuit and/or the second resonant circuit. All such combinations are within the scope of this invention. For example, the inductor of the first resonant circuit may be an air-core inductor and that of the second resonant circuit may be a saturable-magnetic-core inductor. Alternatively, the inductor of the first resonant circuit may be a saturable-magnetic-core inductor and the inductor of the second resonant circuit may be an air-core inductor. It is also within the scope of this invention that the inductor of the first resonant circuit may be a saturable-magnetic-core inductor and that of the second resonant circuit may be a saturable-magnetic-core inductor.

The pulse generator of the instant invention may be configured such that the resonant frequency of the first resonance circuit and the resonant frequency of the second resonance circuit are substantially the same. The pulse generator of the instant invention may also be configured such that the resonant frequency of the first resonance circuit and the resonant frequency of the second resonance circuit are substantially different.

The switch of the pulse generator of the instant invention may have a turn-on time of less than 100 nanoseconds. This switch may be a metal-oxide semiconductor field effect transistor (MOSFET) switch, integrated gate bipolar transistor (IGBT) switch, bipolar junction transistor (BJT) switch, silicon controlled rectifier (SCR) switch, gas discharge switch, or combinations thereof.

The pulse generator of the instant invention may further comprise a current limiting resistor configured to limit damage to the pulse generator circuit. This pulse generator may also further comprise a transformer configured to isolate the pulse generator circuit. This pulse generator may even further comprise a terminating resistance in parallel with the diode that is configured to protect the output stage of the pulse generator.

The pulse generator of the instant invention may be configured to generate at least one pulse that is having a length of no more than 100 nanoseconds at the full-width-at-half-maximum and an amplitude of at least 1 kilovolt.

This pulse generator may be used for electroperturbation of biological cells and also in treatment of human cells and tissue including tumor cells, such as basal cell carcinoma, squamous cell carcinoma and melanoma.

DETAILED DESCRIPTION OF ILLUSTRATIVE EMBODIMENTS

This invention relates to a pulse generator circuit for delivering a short high current pulse to a load. This pulse generator may include a junction recovery diode, a switch, a first resonant circuit and a second resonant circuit. This pulse generator may be used for electroperturbation of biological cells. This pulse generator may be used in treatment of human cells and tissue including tumor cells, such as basal cell carcinoma, squamous cell carcinoma and melanoma.

The components of the electric circuit may be configured as follows. The diode may be configured to store charges in its depletion layer when there is a forward flow of a current and to rapidly switch open after the depletion layer is substantially discharged by a reverse flow of a current. The first resonant circuit may be configured to store energy from a source when the switch is opened and to provide the forward flow of the current through the diode when the switch is closed, thereby charging the depletion layer of the diode. The second resonant circuit may be configured to store the energy transferred from the first resonant circuit after the switch is closed and to provide the reverse flow of the current through the diode until the depletion layer of the diode is substantially discharged, thereby causing the diode to rapidly switch open, and thereafter to provide a reverse current to the load.

Figure 1:
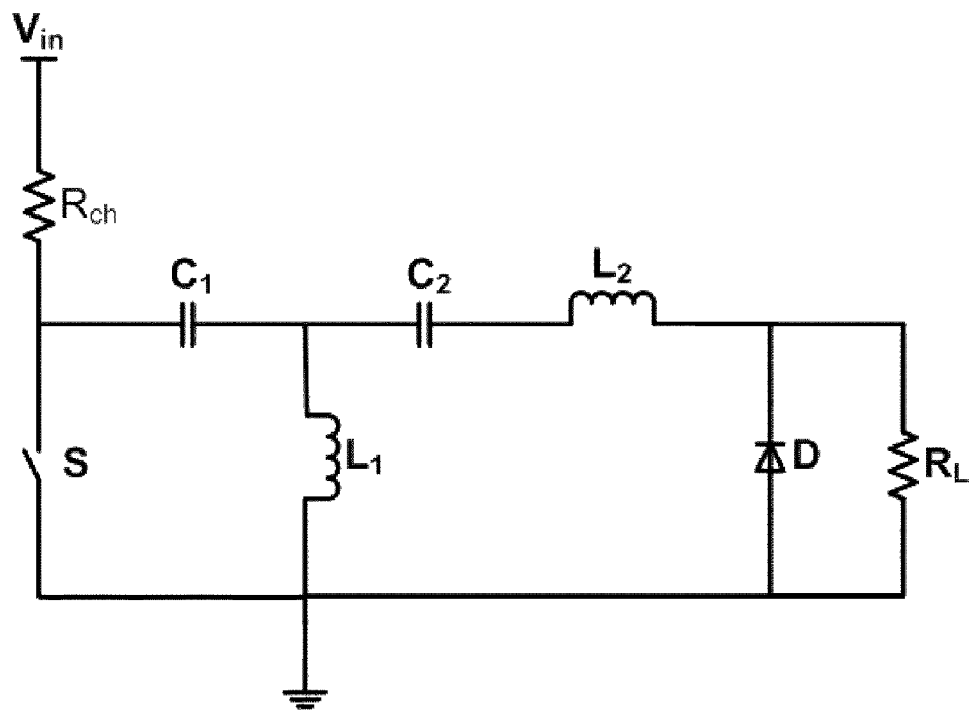
FIG. 1 illustrates an example of the pulse generator of the instant invention.

FIG. 1 schematically shows a simplified pulse generator of the instant invention by way of example. In this pulse generator, the diode D may be configured to operate as an opening switch. The first resonant circuit comprises a first capacitor $C_1$ and a first inductor $L_1$, and the second resonance circuit comprises a second capacitor $C_2$ and a second inductor $L_2$.

In this example, this pulse generator circuit may be connected to a power source depicted as $V_{in}$ through a resistor $R_{ch}$. The pulse generated by the pulse generator of the instant invention may be transferred to a resistive load depicted as $R_L$. This load may be a tumor cell.

At the beginning of a pulse cycle, the switch S may be opened. This may allow the capacitance $C_1$ to be substantially charged by the power source $V_{in}$. After the capacitance $C_1$ is substantially charged, the switch S may be closed. This may cause charges to transfer from the capacitance $C_1$ to the capacitance $C_2$ and thereby forming a forward flow of current through the diode D. During this transfer, the current through the circuit may rise and fall in approximately a sinusoidal manner. This current may cause the diode D to be forward-biased as it travels through it. During this process, charges may be stored in the depletion layer of the diode D.

After the capacitance $C_2$ is charged, the current flow may reverse due to the second resonant circuit. Since the depletion layer of the diode D is charged, the reverse current may flow through the diode D for a period of time. The reverse current flow eventually may substantially discharge the diode D and may result in an abrupt rise in its resistance. This sudden resistance rise occurring in a very short period of time may prevent further flow of the current in the reverse direction through the diode D and may provide the energy stored in the inductor $L_2$ to the load $R_L$ in the form of an electrical pulse.

After the pulse is delivered to the load $R_L$ the switch S may be opened to charge the capacitor $C_1$ to initiate another pulse cycle. Thus, the pulse generator of the instant invention may deliver one pulse or more than one pulse repetitively.

During the pulse delivery process, the diode D may act like a switch. That is, when there is a forward current, it may allow the current to pass through the circuit in forward direction, thereby acting like a switch that is closed. When the current is reversed, it may allow a reverse current through its cathode and anode for a period of time. Then, the diode may prevent this reverse current after its depletion layer is substantially discharged, thereby acting like a switch that is opened.

A diode that can allow this reverse current for a period of time and can prevent the reverse current after this period of time within a very short duration of time is within the scope of this invention. The period of time during which a reverse current is allowed through the diode D is called the "junction recovery time" hereafter. The duration of time, occurring after the junction recovery time, during which the resistance of the diode D substantially increases, thereby preventing the further flow of current, is called the "snap-off time". A diode that can have a suitable junction recovery time and a very short snap-off time is within the scope of this invention. For example, the diode of the instant invention may have a junction recovery time longer than 10 nanoseconds. The junction recovery time may even be longer than 25 nanoseconds. The snap-off time may be shorter than 10 percent of the junction recovery time. For example, the junction recovery time may be shorter than 2.5 nanoseconds or even shorter than 1 nanosecond. This may be a diode that can store charges in its depletion layer with an amount higher than one micro-coulomb.

The diodes of the instant invention may be substantially charged during the forward current flow within a period of time, which is called the "diode saturation time" hereafter. Suitable diodes may be substantially charged within a reasonably short diode saturation time. A suitable diode saturation time may be shorter than 100 nanoseconds.

Examples of such diodes are junction recovery diodes, junction recovery drift diodes, snap recovery diodes, opening switch diodes, step recovery diodes or the like. They are all within the scope of this invention. Such diodes are going to be called as the "junction recovery diodes" hereafter. The junction recovery diodes may have two different principle modes of operation. The first mode is called junction recovery (JR) mode. When operated in this mode, the diodes stop conducting due to recovery of the PN-junction blocking capability. The second mode is called silicon opening switch (SOS) mode. For this mode, the junction does not recover, but the majority of the current is provided to the load $R_L$ due to a drastic increase in resistance of the low-doped part of the P-layer.

The junction recovery diodes operating in the JR mode may have a shorter snap-off time and dissipate less energy during the switching process. However, the JR mode diodes may not be able to switch as high energies as the SOS mode diodes can. Some applications of the pulse generators of the instant invention may require shorter snap-off times. For such applications relatively low energy pulses may be sufficient. Such pulse generators may use the JR mode diodes. For other applications, that require higher energy pulses, but still tolerate longer snap-off times, the SOS mode diodes may be used. Yet for some applications, the JR mode diodes may be used in combination with the SOS mode diodes to remedy the shortcoming of each diode type. Thus, the JR mode diodes, the SOS mode diodes and combinations thereof are all within the scope of this invention.

The junction recovery diodes may be custom designed and manufactured to suit requirements of the instant invention. These diodes may also be chosen among commercially available diodes. Not every commercially available diode may be used to construct the pulse generator of the instant invention. To use a commercial diode that is suitable as a junction recovery diode, several commercially available diodes may be purchased and then experimentally tested for their junction recovery time and snap-off time. The commercial diodes that are found by experimentation to have a suitable junction recovery time and a very short snap-off time may be used in the construction of the pulse generators. There might be many examples of such commercial diodes. One example of such diode is commercially available from EIC Semiconductor (Irwindale, Calif.) with a model number EIC CN25M diode, which has a DC rating of about 1 kilovolt (kV) and about 25 amperes. The junction recovery time for this diode is about 50 nanoseconds. Another example of such diodes is commercially available from Vishay (Shelton, Conn.) with a model name MURS360, which is rated at about 600 V and about 3 amperes and which has about 75 nanoseconds junction recovery time.

One or more than one diode may be used in the construction of the pulse generator. For example a diode array may be used as the junction recovery diode D. The diode array may comprise more than one diode in parallel and/or more than one diode in series. Connecting diodes in parallel may distribute the forward current across the diodes in the array, thus increasing the amount of time that current may be sent through the array before the diodes become fully charged, i.e. saturated. Connecting diodes in series (i.e. diode stack) in an array may increase the amount of voltage that may be applied to the diodes when the current flow is reversed, that is the diodes are reverse-biased. This may allow the output voltage of the pulse generator to be greater. The number of diodes that are placed in parallel and/or in series may be any number, so long as at least one diode is used. Using too many diodes may increase the capacitance of the circuit and slow its performance.

Figure 2:
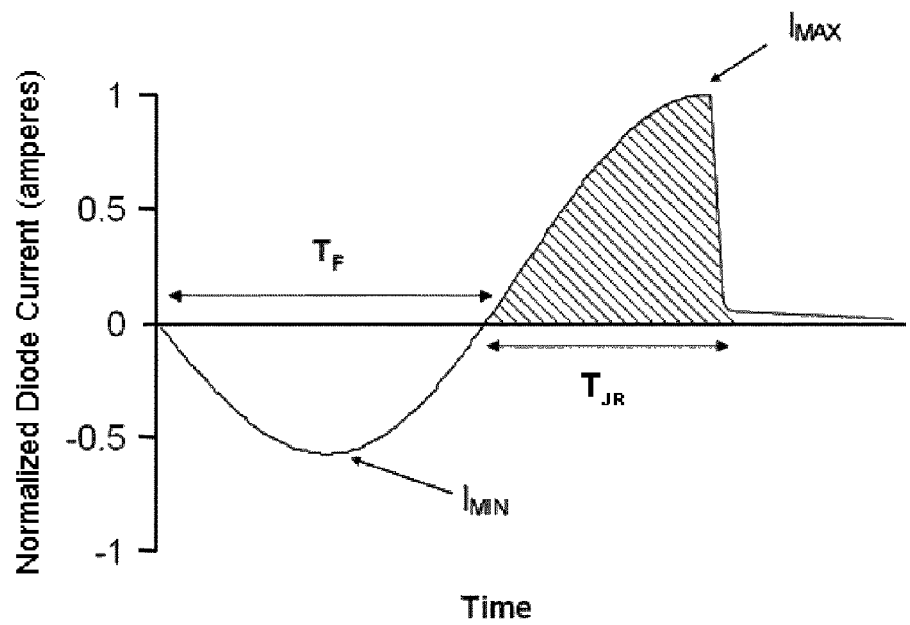
FIG. 2 illustrates the forward current flowing through the diode D for a period of $T_F$ and the reverse current flowing through the diode for a period of $T_{JR}$.

In order to use the diode D as an opening switch and to be able to deliver maximum energy to the load $R_L$, it may be forward and reverse pumped by an appropriate sinusoidal current to ensure that it quits conducting when the majority of the total energy is stored in $L_2$. FIG. 2 illustrates the appropriate current waveform that may flow through the diode D to provide a proper operation. During the forward flow of current, i.e. the forward pumping period, $T_F$, the diode D may be forward biased and charges may be stored in its depletion layer. As explained above, once the current has reversed, and the charges are washed out of the junction, i.e. at the end of the junction recovery time, the diode D may stop conducting and the reverse current flowing through the diode may be provided to the load $R_L$. The junction recovery time is shown as $T_{JR}$ in FIG. 2. The snap-off time may be very small as compared to the junction recovery time and not identified in FIG. 2.

If the diode D switches open when the reverse current is at a maximum, the shaded area under the curve in FIG. 2 may be equal to the area under the curve during the forward pumping period, $T_F$. For this condition, the reverse current peak $I_{MAX}$ may be twice the forward current peak $W_{IN}$. Or in other words, the ratio of the peak of the reverse current to the peak of the forward current or the current ratio=$I_{MAX}/I_{MIN}$ may be two. The pulse generators that are configured to have the current ratio of two are within the scope of this invention.

However, construction of a pulse generator configured to have the current ratio of two may increase its production and operation costs. These costs may be decreased by having pulse generators configured to have the current ratio substantially approaching two. These costs may also be decreased by having pulse generators configured to cause the charges stored in the depletion layer of the diode to be discharged when the energy stored in the second resonant circuit is substantially higher than the energy stored in the first resonant circuit.

For example, the values of circuit components forming the pulse generator shown in FIG. 1 may be selected so as to cause the charge in the diode D to be depleted at approximately the peak of the reverse bias current during the second half of the pulse cycle. When this occurs, the current through the load $R_L$ may be at maximum at the moment the diode D switches open, thus maximizing the peak voltage across the load $R_L$. In one example, to affect this peak timing, the values of capacitances $C_1$ and $C_2$ may be chosen to be substantially the same and the inductances $L_1$ and $L_2$ may be chosen to be substantially the same.

Furthermore, the resonant frequency of both resonant circuits may be substantially the same. Such frequencies are within the scope of this invention. There might be other values for capacitances and inductances of the resonant circuits for which the resonant frequencies of these circuits might be different. Such resonant frequencies are also within the scope of this invention.

Any type of inductor may be used in construction of the pulse generator. For example, air-core type inductors, linear-magnetic-core type inductors (i.e. inductors with magnetic-cores that are operated within the linear region of their hysteresis curve), saturable-magnetic-core type inductors or their combinations may be used. The air-core inductors or the linear-magnetic-core inductors may have several advantages over the saturable-magnetic-core inductors. The air-core inductors or the linear-magnetic-core inductors allow the adjustment of the pulse amplitude independent of the pulse length. The air-core inductors or the linear-magnetic-core inductors are also free of the jitters, which are pulse to pulse variations of pulse amplitude or period, caused by having saturable-magnetic-cores. As a result, a simpler and smaller pulse generator may be constructed by using the air-core inductors or the linear-magnetic-core inductors. However, it might be difficult to scale-up the pulse generators that use the air-core inductors or the linear-magnetic-core inductors to operate relatively higher voltages and deliver higher energy pulses. Although the higher voltage pulse generators may be constructed by using the air-core inductors or the linear-magnetic-core inductors, they may require more complicated circuitry at relatively higher voltages.

The saturable-magnetic-core inductors may have several advantages over the air-core inductors or the linear-magnetic-core inductors. They may be very suitable for construction of higher voltage pulse generators because of their ability to switch relatively higher currents. They may repeatedly achieve higher current operation with relatively less degradation in their performance. However, they may also have disadvantages. For example, the saturable-magnetic-core inductors may introduce amplitude jitter that may be attributed to the BH hysteresis inherent to their magnetic cores. Adding a constant core bias may mitigate the jitter; however this extra circuitry may increase complexity of the pulse generator and may reduce overall efficiency.

Thus, the air-core inductors, the saturable-magnetic-core inductors and the saturable-magnetic-core inductors are all have advantages as well as disadvantages as compared to each other. In some applications, which require pulse generators with relatively free of jitter and with simpler and smaller constructions, but tolerate lower energy pulses, the air-core inductors or the linear-magnetic-core inductors may be used. In other applications, which require higher energy pulse generators, but afford more complex circuitry, the saturable-magnetic-core inductors may be used. Yet in other applications, the air-core inductors, the linear-magnetic-core inductors and the saturable-magnetic-core inductors may be used in combination to remedy the shortcomings of each inductor type when used alone.

Thus, the air-core inductors, the linear-magnetic-core inductors, the saturable-magnetic-core inductors and combinations thereof may be used in the construction of the pulse generators of the instant invention. For example, the inductor of the first resonant circuit may be an air-core inductor, a linear-magnetic-core inductor, a saturable-magnetic-core inductor or combinations thereof. Similarly, the inductor of the second resonant circuit may be an air-core inductor, a linear-magnetic-core inductor, a saturable-magnetic-core inductor or combinations thereof. For example, the inductors $L_1$ and $L_2$ may be both air-core inductors. They may also be both saturable-magnetic-core inductors. Or, $L_1$ may be an air-core inductor and $L_2$ saturable-magnetic-core inductor. Or, $L_1$ may be a saturable-magnetic-core inductor and $L_2$ may be an air-core inductor. Thus, all possible combinations of these inductor types are useful for construction of the first inductor and/or the second inductor of the pulse generators of the instant invention and they are all within the scope of this invention.

In order to create very short pulses, the switch S may need to open and close very quickly. Thus, any switch that can open and close very quickly is suitable for the pulse generator of the instant invention. Examples of such switches may be metal-oxide semiconductor field effect transistor (MOSFET) type switches, (silicon controlled rectifier) SCR type switches, bipolar junction transistor (BJT) type switches, integrated gate bipolar transistor (IGBT) type switches, gas discharge type switches and combinations thereof. Even mechanical relays may be used to construct the switch S.

Any type of MOSFET switch may be used. For example, a MOSFET manufactured by Microsemi Corporation (Irvine, Calif.) with a model number APT37M100L MOSFET and with a DC rating of 1,000 V and 37 amperes may be used as the switch S. The MOSFET may be driven by any suitable power supply (not shown in FIG. 1).

Figure 3:
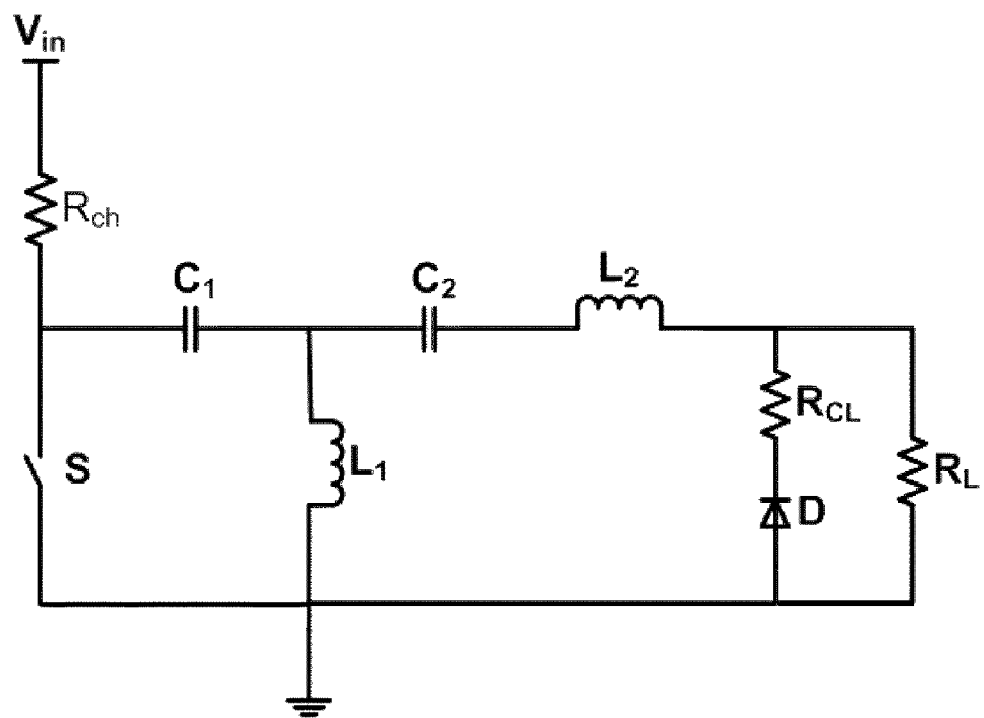
FIG. 3 illustrates an example of the pulse generator of the instant invention.

The pulse generator of the instant invention may include a current limiting resistor $R_{cl}$ configured to limit damage to the pulse generator circuit. This construction of the pulse generator is illustrated in FIG. 3 by way of example. In this example, the current limiting resistor $R_{cl}$ is configured to protect the diode D. This current limiting resistor $R_{cl}$ may be configured to limit damage to any component of the pulse generator.

For example, the current flowing through a diode array may not be evenly distributed among the diodes. This might be due to imperfectly manufactured components of the pulse generator or even imperfectly manufactured pulse generator. This might also be due to current or voltage fluctuations occurring during the operation of the pulse generator. If the current is not evenly distributed among the diodes forming the array, one of these diodes may fail, eventually damaging the whole array or the pulse generator. To prevent such damages a current limiting resistor may be connected in series to each diode or each diode stack.

Figure 4:
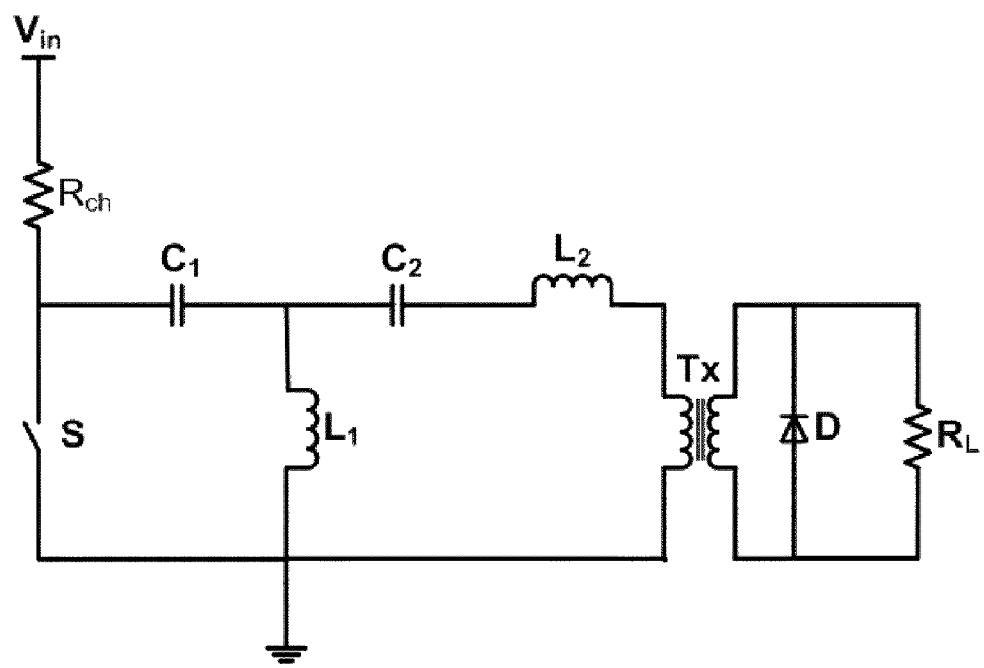
FIG. 4 illustrates an example of the pulse generator of the instant invention.

The pulse generator of the instant invention may include a transformer $T_x$ configured to isolate the pulse generator circuit. This construction of the pulse generator is illustrated in FIG. 4 by way of example. The accidental discharge of electricity, for example to a living body, from the pulse generator is prevented by using this transformer.

Figure 5:
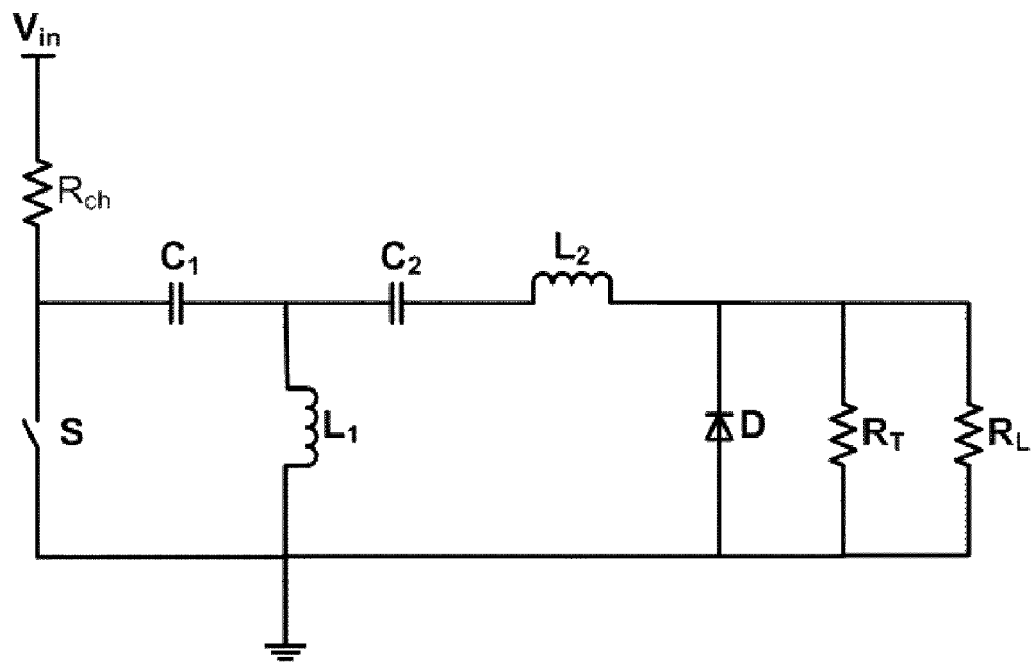
FIG. 5 illustrates an example of the pulse generator of the instant invention.

The pulse generator of the instant invention may include a terminating resistance $R_T$ in parallel with the diode D configured to protect the output stage of the pulse generator. This construction of the pulse generator is illustrated in FIG. 5 by way of example. If the load $R_L$ becomes too high, the terminating resistance $R_T$ may serve to lower the load impedance seen by the output stage (for example, by the diode D) thereby limiting over voltages and protecting the circuit. Value of this resistance may be any value that can protect the circuit without excessively limiting the output pulse characteristics. For example, the value of the terminating resistance may be equal to or many times higher than anticipated level of the load $R_L$. For example, the value of the terminating resistance may be higher than 10 ohms. For example, the value of the terminating resistance may be as high as 10 kilo-ohms.

The pulse generator of the instant invention may include the current limiting resistor $R_{cl}$, the transformer $T_x$ and the terminating resistance $R_T$ alone or in combination. For example, the pulse generator may include a current limiting resistor $R_{cl}$ and a transformer $T_x$. In another example, the pulse generator may include a current limiting resistor $R_{cl}$, a transformer $T_x$ and a terminating resistance $R_T$. All such combinations are within the scope of this invention.

The pulse generators of the instant invention may generate at least one pulse that is having a length of no more than 100 nanoseconds at the full-width-at-half-maximum (FHWM) and an amplitude of at least 1 kV. These generators may deliver pulses with FHWMs varying in the range of 2 nanoseconds to 10 nanoseconds. They may even deliver pulses with FHWMs varying in the range of 2 nanoseconds to 5 nanoseconds. The pulse amplitude of these generators can be scaled with the input voltage $V_{in}$. For example, they can provide pulse amplitudes in the range of 0.5 kV to 7.0 kV by increasing the input voltage $V_{in}$ in the range of 100 V to 1000 V.

Even higher amplitudes may be reached by designing a more complicated switch array, such as a Marx array, that will allow higher current and voltage ratings. In this way, the output amplitude may be scaled to a level even higher than 7.0 kV. The upper amplitude level may be limited by electric breakdown strength of insulators, parasitic capacitance and inductance associated with the switch bank and/or similar electrical problems.

The pulse generators of the instant invention may include electrodes to deliver one or plurality of pulses to biological cells such as human cells and tissue including tumor cells, such as basal cell carcinoma, squamous cell carcinoma and melanoma.

The invention is illustrated further by the following additional examples that are not to be construed as limiting the invention in scope to the specific procedures or products described in them.

Example 1

Resonant Network Design

In this example, the values of the capacitors and inductors may be determined by using a mathematical model for the circuit shown in FIG. 1 as follows. The diode D may be approximated as lossless with a given junction recovery time of about 50 nanoseconds. Then, the forward biased diode may be modeled as an ideal voltage source with a voltage equal to the forward voltage of the diode. This model may be valid until the reverse current flows through the diode for a period equal to the junction recovery time. At this time the conductivity of the lossless diode instantaneously may go to zero. Since the forward biased diode may be modeled as having zero impedance, the diode may be replaced by a short circuit to derive a mathematical model for the current. This expression may be used as a guide to choose inductance and capacitance values that produce an appropriate current to ensure proper switching of the diode (i.e. substantially satisfying $I_{MAX}=2*I_{MIN}$). The following equation was derived by solving for the short circuit current's step response in the s-domain and then using an inverse Laplace transform to obtain a time-domain expression:

$$i_{sc}(t) = \frac{V_o}{kL_1}\left[\frac{\omega_1 \sin(\omega_1 t) - \omega_2 \sin(\omega_2 t)}{\omega_1^2 - \omega_2^2}\right] \quad (1)$$

$$\omega_1^2 = \frac{\omega_o^2}{2kn}\left[1 + n(1+k) + \sqrt{(kn)^2 + 2kn(n-1) + (n+1)^2}\right] \quad (2)$$

$$\omega_2^2 = \frac{\omega_o^2}{2kn}\left[1 + n(1+k) - \sqrt{(kn)^2 + 2kn(n-1) + (n+1)^2}\right] \quad (3)$$

$$\omega_o = \frac{1}{\sqrt{L_1 C_1}} \quad (4)$$

where $i_{sc}$ is the current flowing through the diode, wherein the diode is approximated as a short circuit, $V_o$ is the initial voltage stored in the first capacitor $C_1$, k is the ratio $L_2/L_1$, and n is the ratio $C_2/C_1$.

When the diode quits conducting, it may be important not only that the peak current is maximized, but also that the majority of the energy initially stored in the capacitor $C_1$ is transferred to the inductor $L_2$. If energy remains in the other inductor or capacitors, then it may continue to resonate in the system and will be dissipated into the load $R_L$ some time after the pulse is delivered. To prevent this, the values of the circuit components are chosen such that the energy stored in inductor $L_1$ and capacitors $C_1$ and $C_2$ is at a minimum when the diode stops conducting. The following equations may be used to find the energy stored in different circuit components when the diode stops conducting:

$$i_{L1}(t) = \frac{V_o}{L_1}\left[\frac{\omega_2\left(\omega_1^2 - \frac{\omega_0^2}{nk}\right)\sin(\omega_1 t) + \omega_1\left(\frac{\omega_0^2}{nk} - \omega_2^2\right)\sin(\omega_2 t)}{\omega_1\omega_2(\omega_1^2 - \omega_2^2)}\right] \quad (5)$$

$$v_{L1}(t) = V_o\left[\frac{\omega_2\left(\omega_1^2 - \frac{\omega_0^2}{nk}\right)\cos(\omega_1 t) + \left(\frac{\omega_0^2}{nk} - \omega_2^2\right)\cos(\omega_2 t)}{\omega_1^2 - \omega_2^2}\right] \quad (6)$$

$$v_{L2}(t) = V_o\left[\frac{\omega_1^2\cos(\omega_1 t) - \omega_2^2\cos(\omega_2 t)}{\omega_1^2 - \omega_2^2}\right] \quad (7)$$

where $L_i$ is the current through $L_1$, $V_{L1}$ is the voltage across $L_1$, and $V_{L2}$ is the voltage across $L_2$; $\omega_1$, $\omega_2$, and $\omega_0$ are given by equations 2, 3, and 4 respectively. By using above equations, the instantaneous energy stored in both inductors and both capacitors can be determined. These equations can simultaneously be solved with equation 1 to ensure that the majority of energy is stored in $L_2$ when the diode switches open.

Figure 6:
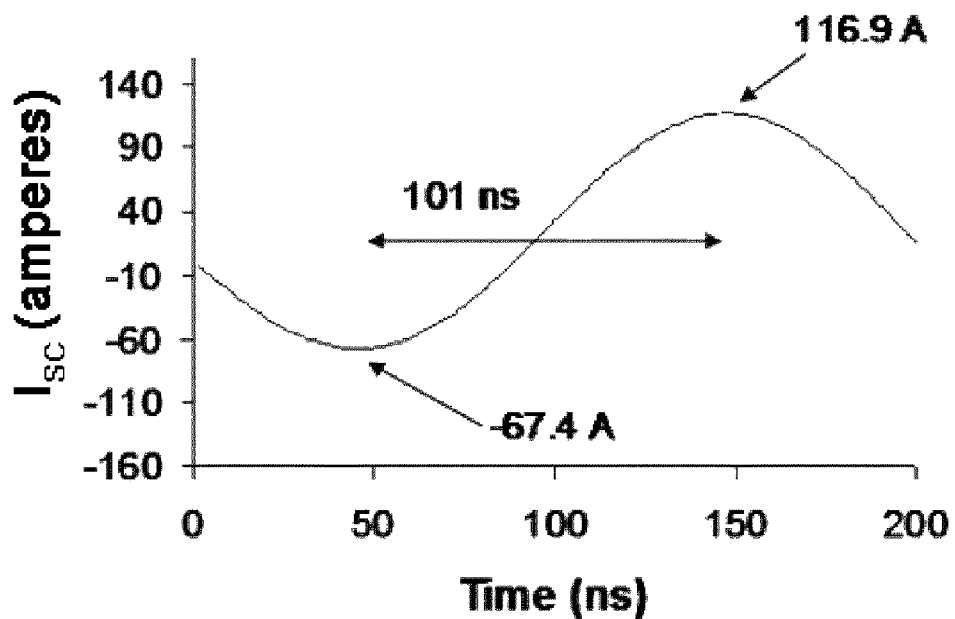
FIG. 6 shows the variation of the calculated short circuit current with time.

A commercially available mathematical software, MAT-LAB was used to solve above equations. The results are schematically shown in FIG. 6. For the junction recovery time of about 50 nanoseconds, for $I_{MAX} \approx 2*I_{MIN}$ and for the capacitors and inductors with the same values, it was determined that $L_1 = L_2 =$ about 260 nanoHenry (nH) and $C_1 = C_2 =$ about 12 nanoFarad (nF). With these values, it may take about 101 nanoseconds for the circuit to go through an $I_{MIN}$ of −67.4 amperes and reach an $I_{MAX}$ of 116.9 amperes. The absolute ratio $I_{MAX}/I_{MIN}$ was determined to be about 1.73. These conditions may be sufficient for the diode to switch near the peak of the reverse current.

Example 2

Switch S

In this example, a variety of solid state switches were tested to determine a switch that may be suitable to use for the construction of the pulse generator of the instant invention. Five different commercially available switches were purchased: one IGBT type switch (rated at 60 amperes, model number GPS60B120KD) from International Rectifiers (El Segundo, Calif.); three MOSFET type switches (first one rated at 13 amperes, model number APT13F120B; second one rated at 28 amperes, model number APT135B2FLL; and third one rated at 37 amperes, model number APT37M100L) from Microsemi Corporation (Irvine, Calif.); and one SCR type switch (model number SK065K) from Littelfuse (Chicago, Ill.). These switches were evaluated by constructing a circuit shown in FIG. 1 with $L_1 = L_2 =$ about 250 nH and $C_1 = C_2 =$ about 12 nF. The diode D was replaced with a short wire. The short circuit current was measured with a current transformer. The peak of the forward current was recorded for each switch, and plotted against the input voltage.

Figure 7:
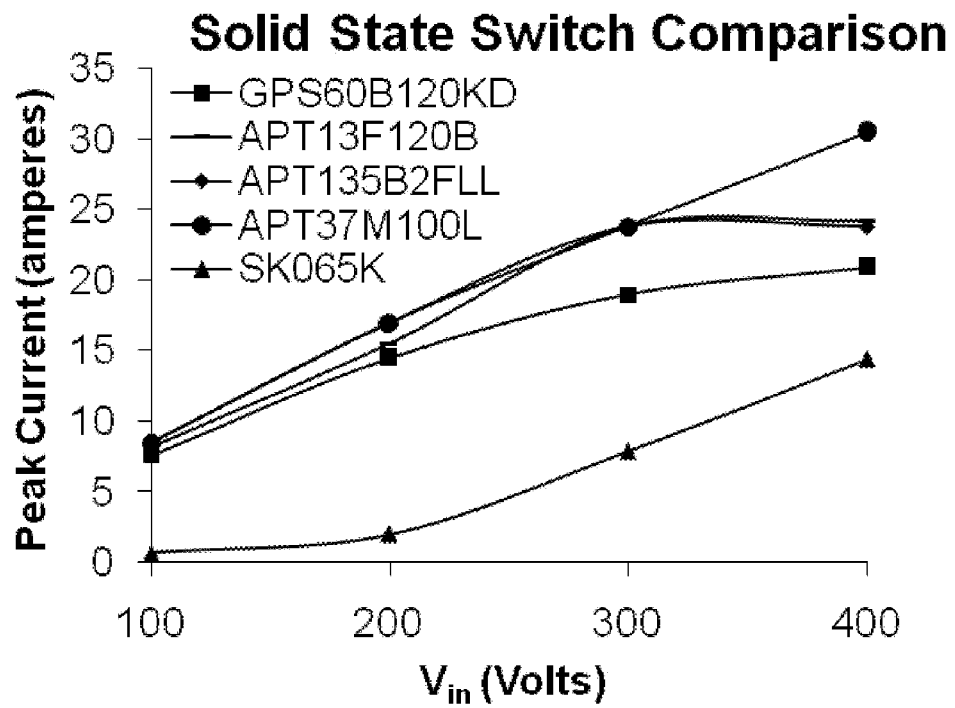
FIG. 7 compares variation of the peak current of five commercial switches that may be used as the switch S with the input voltage.

The results are shown in FIG. 7. APT37M100L MOSFETs (about 1 kV, about 37 amperes DC rated) manufactured by Microsemi Corporation operated linearly with up to an input of about 400 V. Thus this switch performed better than other switches and may be used to construct the pulse generator. The maximum "on" channel resistance of this MOSFET is about 0.33 ohm. It was determined that each switch can handle a half sine wave with about 100 nanoseconds duration and a peak of about 75 amperes before the specified "on" resistance becomes significantly higher.

The turn-on time of the switches is limited by the MOSFET gate capacitance, which is about 10 nF. To charge up this large capacitance, an about 9 amperes MOSFET driver IC was used for each switch. Since the input capacitance was high, trace lengths of any wires connecting the drivers to the gates of the MOSFETs were minimized since the inductance inherent to the traces could be sufficiently large to induce a resonant instability when the drivers were triggered. The gate drivers were able to fully charge the input capacitance in about 30 nanoseconds.

In this Example, four MOSFET switches were used in parallel, each with its own driver circuit. The threshold voltage of MOSFETs exhibits a positive temperature dependence, which inhibits current hogging and makes MOSFETs a good solid state switch for parallel operation. For in detail description of such MOSFETs, for example see: Barkhordarian, "Power MOSFET Basics," International Rectifier, El Segundo, Calif.

Example 3

Construction of a Pulse Generator and Pulses Obtained by Using this Generator

In this Example, two pulse generators were designed and built by using the mathematical model described in Example 1. First pulse generator was designed to provide a pulse with a length of about 5 nanoseconds and the other with a length of about 2.5 nanoseconds.

The pulse generators were constructed by using commercially available EIC CN25M diodes or MURS2510 diodes (both about 1 kV, about 25 amperes DC rating). EIC CN25M diodes had about 50 nanoseconds junction recovery time and MURS2510 diodes about 100 nanoseconds. Both diodes had very short snap-off times. To obtain a pulse with an amplitude of about 5.0 kV with a current of about 100 amperes, five diodes were connected in series to form a stack and five of these stacks were connected in parallel, which formed the diode array.

It was determined that, for the 5 nanosecond pulse generator, $L_1 = L_2 =$ about 260 nH and $C_1 = C_2 =$ about 12 nF and that, for the 2.5 nanosecond pulse generator, $L_1 = L_2 =$ about 70 nH and $C_1 = C_2 =$ about 33 nF. The load $R_L$ for this pulse generator was an about 50 ohms surface mount resistor.

The capacitor $C_1$ was charged to the desired input voltage by a high voltage about 6 kW power supply with a model name Xantrex XPR 600-10 600V. Four APT37M100L MOSFET type switches were used in parallel as the switch S. Each MOSFET switch was driven by an about 9 amperes integrated circuit. These MOSFET drivers were powered by a low voltage about 90 W power supply with a model name Sorenson LS 30-3 30V. The pulse generator was triggered by an Agilent 33120A waveform generator. The output pulse was monitored by Tektronix DPO 4104 1 GHz oscilloscope. The voltage and the current of nanosecond pulses were measured by a power measurement device, which was explained in detail in Krishnaswamy et al., "Compact Subnanosecond High Voltage Pulse Generation System For Cell Electro-Manipulation", U.S. Patent Application No. 2008/0231337 and Sanders et al., "Broadband Power Measurement of High-Voltage, Nanosecond Electric Pulses for Biomedical Applications," IEEE International Power Modulator Conference, Las Vegas, Nev., 2008, pages 350-353. Paragraphs 339 to 363 and FIGS. 44 to 47 of the patent application publication of Krishnaswamy et al. are incorporated herein by reference.

The pulse generators were operated at a repetition rate of about 1 kHz with resistive charging. High repetition rates were not a problem for these pulse generators given the small size of the first capacitor $C_1$. The 6 kW power supply was excessive given that only about 4.32 mJ was needed to charge the capacitor $C_1$= about 12 nF at input voltage of about 600 V. At a repetition rate of about 1 kHz, this energy corresponds to about 4.32 W of average power. With a high current power supply, repetition rates well in excess of 1 kHz may be reached if the charging resistor is replaced with a high current choke or resonant charging network.

Figure 8:
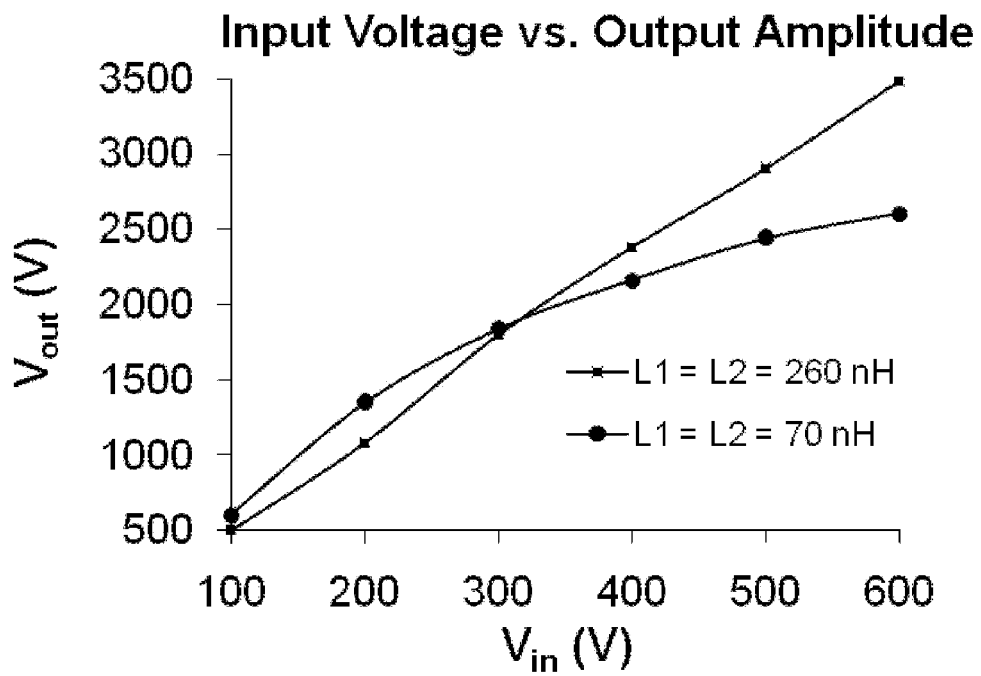
FIG. 8 shows the variation of the pulse amplitude with the input voltage $V_{in}$ for two examples of the pulse generator of the instant invention.

First, the input voltage $V_{in}$ was varied in the range of 100 V to 600 V and the variation of the pulse amplitude $V_{max}$ was measured. Results are shown in FIG. 8. For the pulse generator with the inductances $L_1$=$L_2$= about 260 nH, the pulse amplitude increased somewhat linearly with increasing input voltage. However, for the pulse generator with the inductances $L_1$=$L_2$= about 70 nH, the pulse amplitude increase with input voltage was somewhat non-linear. Particularly for the input voltages above 200 V, the slope of the curve decreased, possibly caused by the losses occurring in the pulse generator.

Figure 9:
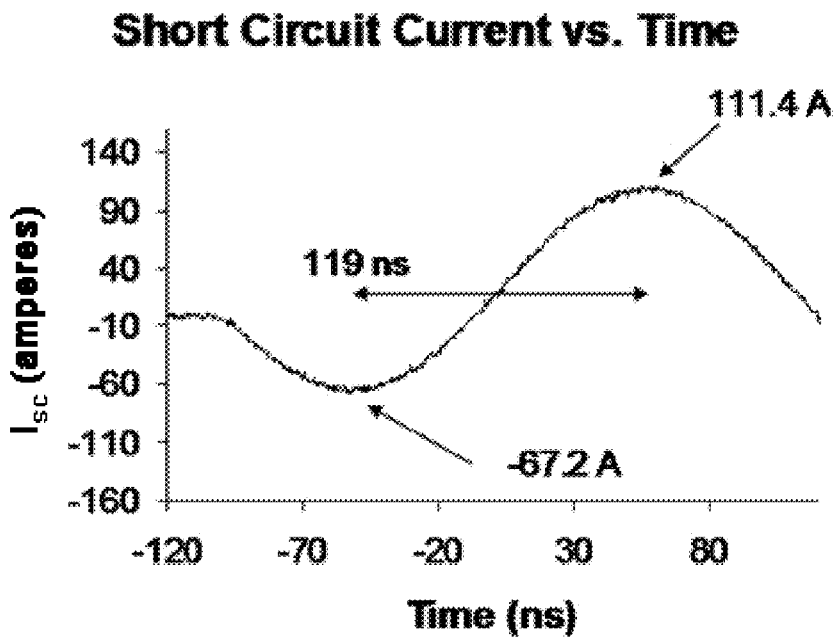
FIG. 9 shows the variation of the measured short circuit current with time.

In order to determine causes of these losses, the short circuit current was measured. This measured current was compared to the short circuit current calculated in Example 1. The results are shown in FIG. 9. The measured current closely matches the calculated current. The period from $I_{MIN}$ to $I_{MAX}$ for the measured current, about 119 nanoseconds was longer than that of the calculated current, about 109 nanoseconds. This discrepancy was probably due to the added inductance of the current transformer used for the measurement. The absolute ratio of $I_{MAX}/I_{MIN}$ for the measured current, about 1.66 was slightly lower than that of the calculated current, about 1.73. This might be a result of the sub-ohm on resistance of the MOSFET switches. The close match of the measured response to the calculated response indicated that the loss in output amplitude was probably caused by the diodes.

The diodes may reduce the pulse amplitude if their junction recovery time is significantly different from the peak (i.e. $I_{MAX}$) time of the reverse current, or if they dissipate a significant amount of the total pulse energy as they turn off.

Figure 10:
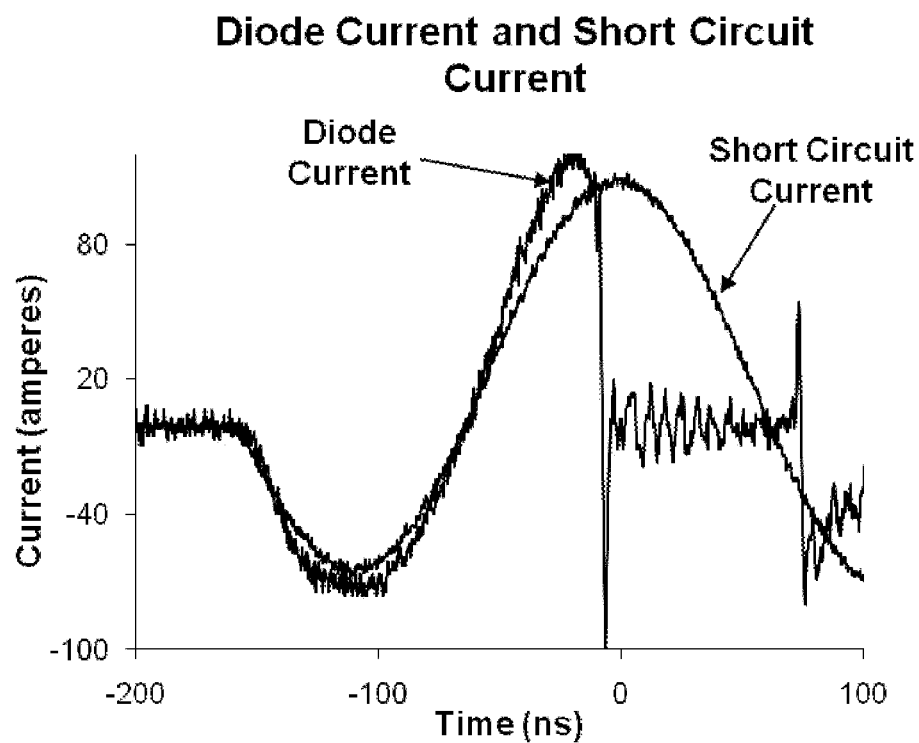
FIG. 10 compares the measured current flowing through the diode with the measured short circuit current.

To determine the cause of the output amplitude loss, the diodes were replaced with a short circuit and the current of this pulse generator was measured. Results of this measurement were compared with measurements of the current flowing through the diodes in FIG. 10. These measurements indicated that the diodes were in fact switching open near the peak of the reverse current. Thus, it was concluded that the loss in amplitude might be a result of energy dissipation during the diode switching process.

Smaller inductance values of $L_1$ and $L_2$ may translate to higher peak currents through the diodes, which would imply that output pulse amplitudes may be increased by manufacturing diodes with reduced energy losses. In practice, after the reverse current through a single diode stack surpasses 50 amperes, the losses in the switching process may increase non-linearly, and the output amplitude may be consequently affected. Even when the current is below 50 amperes per diode stack, the finite rise-time of the pulse may cause the peak amplitude to be significantly less than that calculated by the model described above.

Figure 11:
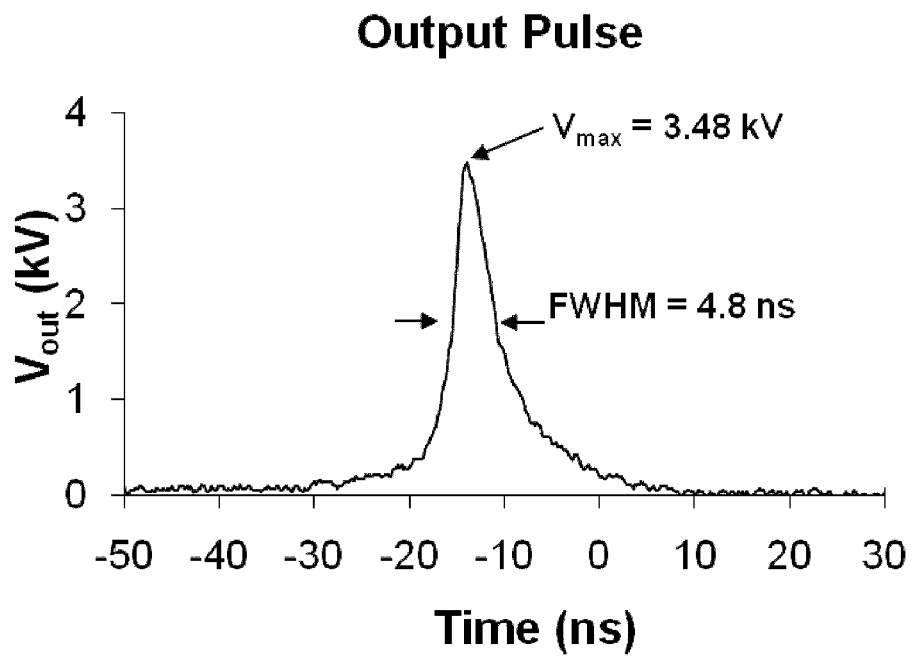
FIG. 11 shows the variation of the output pulse voltage with time.

FIG. 11 shows an output pulse obtained from the pulse generator constructed with the inductances $L_1$=$L_2$=about 260 nH and the capacitances $C_1$=$C_2$= about 12 nF. The input voltage $V_{in}$ was about 600 V and the load $R_L$ was about 50 ohms. The pulse amplitude $V_{max}$ obtained from this pulse generator was about 3.48 kV and the pulse length reported at the full-width-at-half-maximum (FWHM) was about 4.8 nanoseconds. This measured pulse amplitude of about 3.48 kV was about 67% lower than the calculated amplitude of about 5.85 kV, which would have been obtained if the diode losses could be reduced to negligible levels. In spite of this limitation, it was demonstrated that careful choice of inductor and capacitor values may yield a pulse generator with an output amplitude that may scale with the input voltage.

Figure 12:
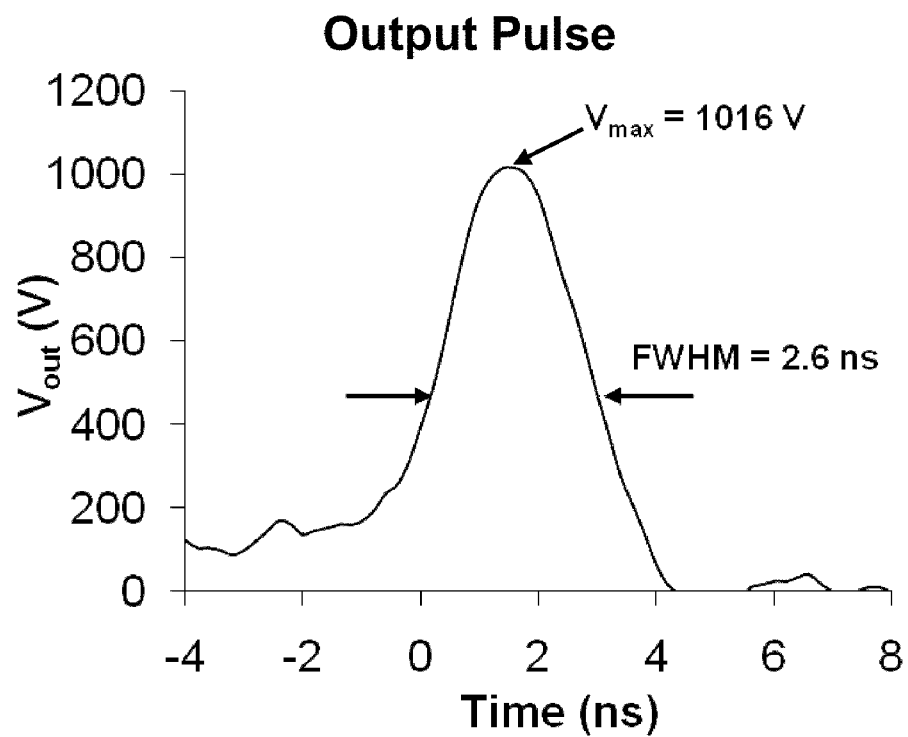
FIG. 12 shows the variation of the output pulse voltage with time.

FIG. 12 shows an output pulse obtained from the pulse generator constructed with the inductances $L_1$=$L_2$= about 70 nH and the capacitances $C_1$=$C_2$= about 33 nF. The input voltage $V_{in}$ was about 600 V and the load $R_L$ was about 50 ohms. The pulse amplitude $V_{max}$ obtained from this pulse generator was about 1.016 kV and the FWHM was about 2.6 nanoseconds.

This example demonstrated that pulses with amplitudes exceeding 1 kV and the FWHMs shorter than 100 nanoseconds may be obtained by having the pulse generators of the instant invention. This example further demonstrated that these pulse generators may provide pulses with amplitudes that may be scaled with the input voltage.

Example 4

Repeatability and Jitter

Figure 13:
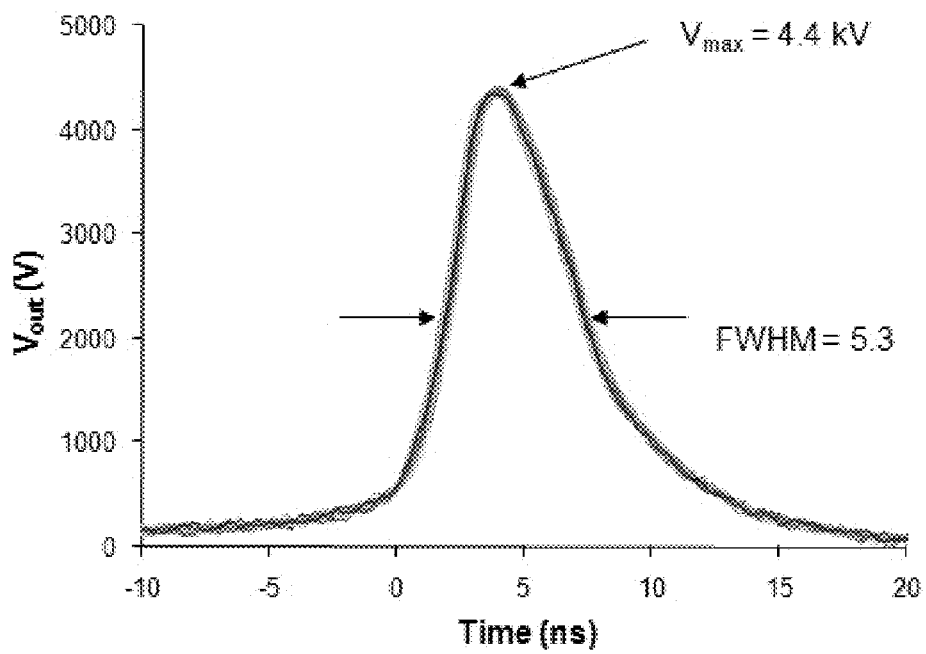
FIG. 13 shows the variation of the output pulse voltage with time for 25 repetitive pulse outputs.

In this Example, the jitter and the repeatability of one of the pulse generators of Example 3 were determined. This pulse generator was constructed with the inductances $L_1$=$L_2$= about 260 nH and the capacitances $C_1$=$C_2$= about 12 nF. The input voltage $V_{in}$ was about 700 V and the load $R_L$ was about 50 ohms. FIG. 13 shows traces of 25 pulses obtained by using this pulse generator. In this figure, the pulse traces were superimposed over one another. The pulse amplitude obtained from this pulse generator was about 4.40 kV and the pulse length reported at the FWHM was about 5.3 nanoseconds.

As these results indicated, there was no recognizable jitter. Pulse to pulse deviation of the amplitude and the FWHM was also negligible. This example demonstrated that the pulse generators of this invention may provide desired pulses repeatedly with negligible jitter and deviation.

Example 5

Input-Output Linearity of the Pulse Generators

In this Example, the input and output linearity of one of the pulse generators of Example 3 were further determined. This pulse generator was constructed with the inductances $L_1$=$L_2$= about 260 nH and the capacitances $C_1$=$C_2$= about 12 nF. The input voltage $V_{in}$ was about 700 V and the load $R_L$ was about 50 ohms.

Figure 14:
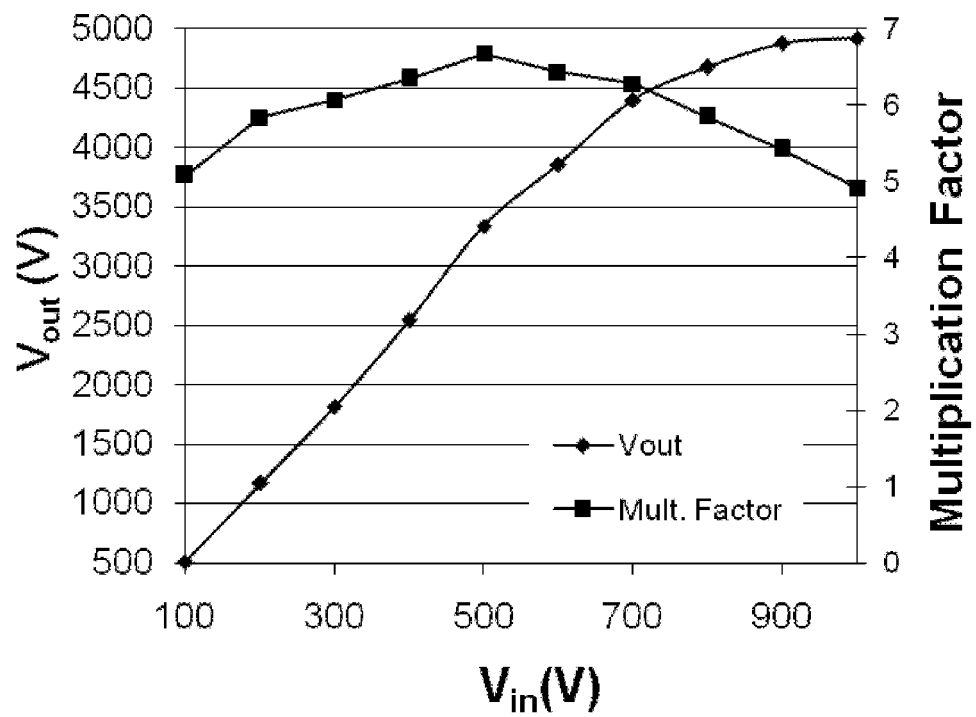
FIG. 14 shows the variation of the pulse amplitude with the input voltage $V_{in}$.

As shown in FIG. 14, the pulse amplitude increased with increasing input voltage. The ratio of the output amplitude to the input voltage (i.e. multiplication factor) increased somewhat linearly with increasing input voltage up to about 500 V. Then, above 500 V, this ratio started to decrease. This decrease may be due to losses from MOSFETs used as switch S. Adding more MOSFETs in parallel to the pulse generator of this example may mitigate this problem.

This example demonstrated that the pulse generators of this invention may provide pulses with amplitudes that may be scaled with the input voltage.

Example 6

Construction of a Pulse Generators

In this Example, a construction of a pulse generator circuit schematically shown in FIG. 1 was demonstrated.

In this construction, the pulse generator includes a junction recovery diode D, wherein the anode side of the diode D is connected to the ground, a second inductor $L_2$ connected to the cathode side of the diode, a second capacitor $C_2$ connected in series with the second inductor $L_2$, first terminal of a first inductor $L_1$ connected to the second terminal of the second capacitor $C_2$, second terminal of the first inductor $L_1$ connected to the ground, first terminal of a first capacitor $C_1$ connected to first terminal of the first inductor $L_1$ as well as the second terminal of the second capacitor $C_2$, first terminal of a switch S connected to the second terminal of the first capacitor $C_1$, second terminal of the switch S connected to the ground. A load $R_L$ may be connected in series with the diode D.

In this construction, every component of the circuit may be a single component or may be an array of the component. For example, the first capacitor $C_1$ may be a single capacitor or a capacitor array. These arrays may be constructed by connecting each component in series and/or in parallel. For example, the capacitor array may be constructed by connecting more than one capacitor in series and/or in parallel.

The components, steps, features, objects, benefits and advantages that have been discussed above are merely illustrative. None of them, including the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

For example, although diodes, capacitances, inductances, resistances and switches have been illustrated in the drawings and/or discussed as single components, they may instead each be made of multiple components, cooperating together to perform the illustrated or recited function.

In short, the scope of protection is limited solely by the claims that now follow. That scope is intended to be as broad as is reasonably consistent with the language that is used in the claims and to encompass all structural and functional equivalents. Nothing that has been stated or illustrated is intended to cause a dedication of any component, step, feature, object, benefit, advantage, or equivalent to the public, regardless of whether it is recited in the claims.

We claim:

1. A pulse generator circuit for delivering a short high current pulse to a load comprising:
    a diode configured to store charges in its depletion layer when there is a forward flow of a current and to rapidly switch open after the depletion layer is substantially discharged by a reverse flow of a current;
    a switch configured to allow storage of energy from a source when it is opened and to allow the forward current flow after it is closed;
    a first resonant circuit configured to store energy from the source when the switch is opened and to provide the forward current flow through the diode after the switch is closed, thereby charging the depletion layer of the diode; and
    a second resonant circuit configured to store the energy transferred from the first resonant circuit after the switch is closed and, solely due to the closure of the switch, to provide the reverse current flow through the diode until the depletion layer of the diode is substantially discharged, thereby causing the diode to rapidly switch open, and thereafter to provide a reverse current to the load; and
    an electrical component configured to limit damage to the pulse generator circuit, wherein said electrical component is selected from a group consisting of a current limiting resistor, a terminating resistance and combinations thereof.

2. The pulse generator circuit of claim 1, wherein the pulse generator is configured to cause the charges stored in the depletion layer of the diode to be substantially discharged when the peak current flowing through the second resonant circuit is substantially higher than the peak current that previously flowed through the first resonant circuit.

3. The pulse generator circuit of claim 1, wherein the pulse generator is configured to cause the charges stored in the depletion layer of the diode to be substantially discharged when the ratio of the peak of the reverse flow of the current to the peak of the forward flow of the current is substantially approaching to two.

4. The pulse generator circuit of claim 1, wherein the diode is configured to operate in a junction recovery mode.

5. The pulse generator circuit of claim 1, wherein the diode is configured to operate in a silicon opening switch mode.

6. The pulse generator circuit of claim 1, wherein the diode has a junction recovery time longer than 10 nanoseconds.

7. The pulse generator circuit of claim 1, wherein the diode has a junction recovery time longer than 25 nanoseconds.

8. The pulse generator circuit of claim 1, wherein the diode is configured to have a snap-off time shorter than 10 percent of its junction recovery time.

9. The pulse generator circuit of claim 1, wherein the diode is configured to store charges in its depletion layer with an amount higher than one micro-coulomb.

10. The pulse generator circuit of claim 1, wherein the first resonant circuit includes a first inductor.

11. The pulse generator circuit of claim 10, wherein the first inductor is at least one of an air-core inductor, linear-magnetic-core inductor, saturable-magnetic-core inductor or combinations thereof.

12. The pulse generator circuit of claim 10, wherein the first inductor is an air-core inductor.

13. The pulse generator circuit of claim 1, wherein the second resonant circuit include a second inductor.

14. The pulse generator circuit of claim 13, wherein the second inductor is at least one of an air-core inductor, linear-magnetic-core inductor, saturable-magnetic-core inductor or combinations thereof.

15. The pulse generator circuit of claim 13 wherein the second inductor is an air-core inductor.

16. The pulse generator circuit of claim 1, wherein the resonant frequency of the first resonance circuit and the resonant frequency of the second resonance circuit are substantially the same.

17. The pulse generator circuit of claim 1, wherein the resonant frequency of the first resonance circuit and the resonant frequency of the second resonance circuit are substantially different.

18. The pulse generator circuit of claim 1, wherein the switch has a turn-on time of less than 100 nanoseconds.

19. The pulse generator circuit of claim 1, wherein the switch is at least one of a metal-oxide semiconductor field effect transistor switch, integrated gate bipolar transistor switch, bipolar junction transistor switch, silicon controlled rectifier switch, gas discharge switch, or combinations thereof.

20. The pulse generator circuit of claim 1, wherein the electrical component configured to limit damage to the pulse generator circuit is a current limiting resistor.

21. The pulse generator circuit of claim 1, wherein the electrical component configured to limit damage to the pulse generator circuit is a terminating resistance.

22. The pulse generator circuit of claim 1, wherein the pulse generator further comprises a transformer configured to isolate the pulse generator circuit.

23. The pulse generator circuit of claim 1, wherein the pulse generator is configured to generate at least one pulse that is having a length of no more than 100 nanoseconds at the full-width-at-half-maximum and an amplitude of at least 1 kV.

24. The pulse generator circuit of claim 1, wherein the first resonant circuit comprises a first capacitor and a first inductor; the second resonant circuit comprises a second capacitor and a second inductor; each of the first capacitor, the first inductor, the second capacitor, and the second inductor has a first terminal and a second terminal; and the first terminal of the first inductor is connected to both the first terminal of the first capacitor and the second terminal of the second capacitor.

25. The pulse generator circuit of claim 24, wherein the pulse generator circuit further comprises a ground; the diode has an anode side and a cathode side; the anode side of the diode is connected to the ground; the first terminal of the second inductor is connected to the cathode side of the diode; and the first terminal of the second capacitor is connected to the second terminal of the second inductor.

26. The pulse generator circuit of claim 25, wherein the second terminal of the first inductor is connected to the ground; the switch has a first terminal and a second terminal; and the first terminal of the switch is connected to the second terminal of the first capacitor and the second terminal of the switch is connected to the ground.

27. The pulse generator circuit of claim 1, wherein the switch is an array of switches configured to act as a single switch, and wherein the single switch is only in closed state or only in opened state.

* * * * *